United States Patent [19]

Waller

[11] Patent Number: 5,214,172

[45] Date of Patent: May 25, 1993

[54] CATALYTIC TRANSVINYLATION OF VINYL ESTERS

[75] Inventor: Francis J. Waller, Allentown, Pa.

[73] Assignee: Air Products and Chemicals, Inc., Allentown, Pa.

[21] Appl. No.: 695,675

[22] Filed: May 6, 1991

[51] Int. Cl.$^5$ .............................................. C11C 3/10
[52] U.S. Cl. .................................... 554/165; 554/167
[58] Field of Search ................. 260/410.9; 554/165, 554/167; 556/137

[56] References Cited

U.S. PATENT DOCUMENTS

| | | | |
|---|---|---|---|
| 2,299,862 | 10/1942 | Toussaint et al. | 260/410 |
| 2,997,494 | 8/1961 | Brown | 260/410.9 |
| 3,000,918 | 9/1961 | Wilip et al. | 260/410.9 |
| 3,188,319 | 6/1965 | Smidt et al. | 260/410.9 |
| 3,560,534 | 2/1971 | MacDonald | 260/410.9 |
| 4,425,277 | 1/1984 | Kawamoto et al. | 260/410.9 |

FOREIGN PATENT DOCUMENTS 0351603 1/1990 European Pat. Off. .
1486443 9/1977 United Kingdom .

OTHER PUBLICATIONS

McKean et al., Tetrahedron, vol. 28, "Pd (11) Catalyzed Vinyl Interchange Section II", pp. 233–38, 1972.
R. L. Adelman, "The Interchange Reaction of Vinyl Acetate with Organic Acids", J. Org. Chem., (1949) 14, p. 1057.
D. Swern, et al., "Vinyl Laurate and Other Vinyl Esters", 30, p. 106, 1950.
H. Hopff et al., "The Vinyl Interchange Reaction", Tetrahedron, 24, pp. 2205 to 2214, and pp. 3887 to 3890, 1968.
F. E. McKeon, et al., "The Palladium (II) Catalyzed Vinyl Interchange Reaction-II", Tetrahedron, vol. 28, pp. 233–238 (1972).
A. A. Ketterling et al., "Carboxylic Acid Transvinylation as Catalysed by Complexes of Palladium Acetate with Phenantroline like Ligands", Applied Catalysis, 66, pp. 123–132 (1990).
N. S. Allen, et al., "Catalytic Reactions Involving Palladium (II) Salts Supported on Amberlyst", Inorg. Chim. Acta. 28, (1978) pp. 231–235.

*Primary Examiner*—Jose G. Dees
*Assistant Examiner*—D. D. Carr
*Attorney, Agent, or Firm*—Mark L. Rodgers; William F. Marsh; James C. Simmons

[57] ABSTRACT

Transvinylation of a vinyl ester with either an alcohol to form a vinyl ether or a carboxylic acid to form a vinyl ester of different molecular weight than the starting ester is catalyzed with a palladium catalyst which is introduced to the reaction mixture as a palladium carboxylate complexed with an aryl N-containing ligand and the activity of this reaction is significantly improved with the addition of a strong acid. Also described are phenanthroline compounds and their novel complexes with palladium acetate which are useful as transvinylation catalysts.

13 Claims, No Drawings

CATALYTIC TRANSVINYLATION OF VINYL ESTERS

FIELD OF THE INVENTION

This invention relates to an improved process for transvinylation of a vinyl ester with either an alcohol or a carboxylic acid using a palladium catalyst complex. In another aspect it relates to a method of increasing the activity of the catalytic transvinylation of vinyl esters and carboxylic acids. In another aspect it relates to phenanthroline derivatives and their novel complexes with palladium acetate which are useful in such catalytic transvinylations.

BACKGROUND OF INVENTION

Catalytic transvinylation of vinyl esters with carboxylic acids to form compounds useful in the manufacture of plastics, as polymeric coatings, adhesives or internal plasticizers is a well known reaction. Early accounts of this process used as a catalyst a mercury salt and a strong acid such as disclosed in U.S. Pat. No. 2,299,862 (1942) and U.S. Pat. No. 2,997,494 (1961). Mercuric sulfate is described as the catalyst for such a reaction in U.S. Pat. No. 3,000,918 (1961) and U.S. Pat. No. 3,560,534 (1971) discloses transvinylation using a catalytic amount of a mercuric salt and perchloric acid. Mercury based transvinylation catalysts are also described in J. Org. Chem. 14, 1057 (1949); Org. Syn. 30, 106(1950); and Tetrahedron 24, 2205 and 3887 (1968), the latter reference stating that with a mercury salt, a strong acid such as sulfuric acid is necessary in the system.

Because of the toxic nature of mercury and mercury salts, considerable effort has been devoted to developing catalyst based upon other metals.

U.S. Pat. No. 3,188,319 (1965) discloses a transvinylation process which avoids the use of mercury by employing a catalyst of palladium acetate or a double chloride such as $PdCl_2 \cdot LiCl$. Because of the toxic character of mercury-based catalyst and the thermal instability of palladium-based catalyst, European Patent Application Publication No. 0,351,603 published January 1990, recommends the use of a ruthenium compound as the catalyst for transvinylation.

The instability of palladium catalysts is discussed by McKeon and Fitton, Tetrahedron 28, 233 (1972) who describe improved catalysts for vinylation of alcohols and carboxylic acids. Two catalysts prepared were diacetato (2,2'-bipyridyl) palladium(II) and diacetato (1,10-phenanthroline) palladium(II). Such catalysts are said to be advantageous because they do not form acetal by products which are observed using catalyst such as the palladium salts of strong acids, for example palladium chloride, which tends to be reduced to palladium metal during the reaction. Vinyl laurate was prepared from lauric acid and vinyl acetate using the palladium acetate complex with 2,2'-bipyridyl.

More recently Ketterline, et al., Applied Catalysis 66, 123 (1990) discussed vinylation of carboxylic acids by vinyl acetate using a catalyst of palladium acetate complexed with di-imine ligands to stabilize the catalyst and avoid its reduction to metallic palladium. Complexes were synthesized using 1,10-phenanthroline and 2,2'-bipyridyl as ligands. Vinylation of propionic acid was carried out with vinyl acetate. Addition of trifloroacetic acid did not change the rate of vinyl propionate production, thus showing no effect of Bronsted acidity.

Other approaches to solve the stability problem are described by U.S. Pat. No. 4,425,277 (1984) in which a binary catalyst system is used formed from a palladium compound supported on a solid carrier such as silica gel or active carbon with a cocatalyst consisting of a combination of an alkali metal compound and a copper(II) compound. Similarly, Allen et al., in Inorg. Chim. Acta., 28 (2), 231 (1978) disclose transvinylation reactions using as a catalyst palladium(II) salts supported on Amberlyst A21. Palladium compounds disclosed include sodium tetrachloro palladium.

A process variation is disclosed in British Patent 1,486,443 (1977) which describes a process for the production of a vinyl ester of an organic carboxylic acid with reactants chosen that the vinyl ester of the organic carboxylic acid has a lower boiling point than the vinyl ester used as an initial reactant. Consequently the product can be separated by distillation of the reaction products. The examples use a catalyst of a palladium chloride-lithium chloride salt or a mercury acetate with copper resinate.

SUMMARY OF THE INVENTION

I have now discovered that the catalytic activity of a palladium carboxylate complexed with one or more aryl N-containing ligands can be improved substantially in the transvinylation of a vinyl ester with either an alcohol or a carboxylic acid by adding to the reaction mixture a sulfur oxy-acid or sulfur oxy-acid mixture having a Hammett acidity ($-H_O$) of greater than 0.8. This reaction is particularly well suited for the transvinylation of mono and multi-substituted basic acids. The invention provides increased transvinylation activity of the catalyst over other catalysts described in the art, where activity is defined as moles of product produced per gram mole of palladium catalyst per unit of time.

I have also discovered two compounds which are believed to be useful in the formation of novel palladium catalysts. These are 5-chloro-1,10-phenanthroline and 2,9-dimethyl-1,10-phenanthroline. Both of these compounds when complexed with palladium acetate are effective in the transvinylation between a vinyl ester and a carboxylic acid.

DETAILED DESCRIPTION OF THE INVENTION

The transvinylation of vinyl ester with an organic acid is an equilibrium controlled reaction. It is desirable to perform the transvinylation reactions with a vinyl ester to organic acid ratio greater than 3. When excess vinyl acetate is employed, it is conveniently used as a solvent. Another method to shift the reaction equilibrium is to continuously remove one of the reaction products. Other solvents that do not interfere with the compatibility of the catalyst, vinyl ester or the organic acid or the activity of the catalyst are suitable. In certain cases, a solvent may be required to enhance the solubility of the organic acid. Transvinylation reactions are conducted at atmospheric or elevated pressures. When the vinyl ester reactant is vinyl acetate, the reaction temperature at atmospheric pressure is up to 72° C., the boiling point of vinyl acetate.

Suitable organic acid reactants are aliphatic and aromatic mono-carboxylic acids and multi-carboxylic acids, including dibasic acids, both aliphatic and aromatic, and tricarboxylic acids.

The transvinylation reaction is normally carried out in the liquid phase but hetergeneous and vapor phase systems can be used. For example, the aryl N-containing ligand for the palladium catalyst can also be part of a polymer support. Suitable polymer supports are crosslinked polyvinylpyridines called Reillex ® available from Reilly Tar and Chemical Company. Another approach to immobilize the N-containing bidentate ligand to a solid carrier is through a silicon anchoring group covalently bonded to the bidentate ligand. See U.S. Pat. No. 4,873,212 (1989). These immobilized forms of the catalyst can be used in the liquid or vapor phase.

The aryl N-containing ligand complexes of palladium carboxylates can be prepared by the general procedure described in J. Chem. Soc. (1965), 3632. In general, palladium acetate complexes are insoluble in refluxing vinyl acetate. Once the mono-basic acids are added for transvinylation, the palladium acetate complexes become soluble. During this initial stage, the palladium acetate is anion exchanged to produce a palladium carboxylate. Alternatively, the aryl N-containing ligand palladium carboxylate and be made directly through the combination of the palladium carboxylate and aryl N-containing ligand in a suitable solvent. The present identity of the catalytic mechansim is not established, but the catalyst is defined, for purposes of this invention, in terms of the materials added to the reaction.

The transvinylation activity of the palladium catalyst precursor can be determined by an IR method that measures the absorbancy ratio of the $\nu_{co}$ of the organic acid to the sum of absorbancies for $\nu_{co}$ of the organic acid and $\nu_{c=c}$ of the higher vinylic ester. Aliquots of the transvinylation reaction solution are evaporated with a $N_2$-stream to remove all the vinyl acetate.

The aryl N-containing ligand complexes of palladium carboxylates did not reduce to palladium metal during reaction conditions. Other palladium compounds tested either reduced to palladium metal or were inert as catalysts for the vinyl-interchange reaction.

The non-bidentate aryl N-containing ligands for the palladium carboxylates, for example, the pyridine ligand, has a strong trans effect and a slow transvinylation activity. During transvinylation conditions, the activity of this catalyst is enhanced by a strong acid. Strong acids are defined for this invention as sulfur oxy-acids or sulfur oxy-acid mixtures, either organic or inorganic, having a Hammett acidity ($-H_o$) of greater than 0.8. Suitable acids are $H_2SO_4$, p-toluenesulfonic acid, Amberlyst ®15 resin, perfluorinated ion-exchange polymers with pendant sulfonic acid groups (ref.: Waller, et al. Chemtech, July, 1987, 438) and the like. The mole ratio of strong acid to the palladium carboxylate complex can vary considerably, but is preferably about 1:1 to 10:1.

Suitable aryl N-containing ligands are: 4,7-diphenyl-1,10-phenanthroline, 5-chloro-1,10-phenanthroline, 1,10-phenanthroline, 3,4,7,8-tetramethyl-1,10-phenanthroline, 2,9,4,7-tetramethyl-1,10-phenanthroline, 2,9-dimethyl-4,7-diphenyl-1,10-phenanthroline, 2,9-dimethyl-1,10-phenanthroline, 2,2'-dipyridyl, 4,4'-diphenyl-2,2'-dipyridyl, 4-methyl-1,10-phenanthroline, 2,2'-biquinoline, 5-nitrophenanyhroline 5-methyl-1,10-phenanthroline, isoquinoline, pyridine and the like. With multi-basic acids, for example di-basic acids, the cis aryl N-containing palladium carboxylates were inactive. The pyridine complex showed low activity. Addition of an optional acid resulted in increased transvinylation activity for the pyridine complex.

The improved series of palladium catalysts for the transvinylation reaction is further illustrated by the following Examples and Comparative Examples. In particular, it should be noted that the aryl N-containing ligands for the palladium carboxylates give transvinylation catalyst precursors that are not subject to reduction to palladium metal. Although not to be bound by theory, since the initially charged palladium acetate complex undergoes an anion exchange with the organic acid, the new palladium carboxylate complexes apparently require additional activation with a strong acid to activate the transvinylation catalyst. This activation process is dependent upon (1) the type of aryl N-containing ligand (cis complexes of palladium carboxylates with bidentate ligands or strong sigma N-donor ligand), (2) chelating or non-chelating ability of the basic organic acid and (3) the basicity of the bidentate aryl N-containing ligand. These correlations to help illustrate the present invention should not limit the scope of the invention.

EXAMPLES

The following examples are given to illustrate the invention and should not be construed as limiting in scope. Activity comparisons were made using stearic acid under a set of standard conditions. All vinylic esters prepared in these examples had properties consistent with structures and published data.

EXAMPLE 1-13

Examples 1-13 demonstrate the preparation of palladium complex catalysts.

General procedure: A round bottom flask equipped with a reflux condenser was charged with solvent(s), palladium acetate and ligand. During a 2-4 hour reaction time at reflux (exceptions noted in Table 1), the color changed from red to yellow. After cooling to room temperature, the complex was isolated by filtration. The complex was washed twice with 10 ml pentane and then dried. Conditions and results are given in Table 1.

TABLE 1

| | Pd(OAc)$_2$ Complexes with Aryl N-containing Ligands | | | | |
|---|---|---|---|---|---|
| Ex | Pd(OAc)$_2$ (mmol) | Ligand (mmol) | Solvent (ml) | Complex (mmol) | Color |
| 1 | 1.02 | 2,2'-biquinoline (1.18) | CH$_3$CN (50) | 0.85 | dark yellow |
| 2 | 2.02 | 2,2'-dipyridyl (2.92) | CH$_3$CN (25) | 1.83 | yellow |
| 3 | 2.32 | pyridine (5.69) | Et$_2$O (15) Toluene (5) room temp. | 2.23 | light yellow |
| 4 | 1.41 | isoquinoline (25.5) | Et$_2$O (5) Toluene (5) | 1.27 | cream |
| 5 | 1.03 | 1,10-phenanthroline (2.27) | CH$_3$CN (25) | 0.80 | yellow |
| 6 | 1.11 | 3,4,7,8-tetramethyl-1,10-phenanthroline (1.61) | CH$_3$CN (25) room temp. | 0.87 | yellow |
| 7 | 0.91 | 2,9-dimethyl-4,7 diphenyl-1,10-phenanthroline (1.13) | CH$_3$CN (25) room temp. | 0.79 | yellow |
| 8 | 1.09 | 4,7-diphenyl-1,10-phenanthroline (1.35) | CH$_3$CN (25) | 0.90 | yellow |
| 9 | 0.99 | 4,4'-diphenyl-2,2'-dipyridyl | CH$_3$CN (25) | N.D. | N.D. |

TABLE 1-continued

Pd(OAc)$_2$ Complexes with Aryl N-containing Ligands

| Ex | Pd(OAc)$_2$ (mmol) | Ligand (mmol) | Solvent (ml) | Complex (mmol) | Color |
|---|---|---|---|---|---|
| 10 | 0.99 | 5-chloro-1,10-phenanthroline (1.19) (1.15) | CH$_3$CN (25) room temp. | 0.69 | light yellow |

(Found: C, 43.29; H, 2.91; N, 6.24. Calc. for C$_{12}$H$_{13}$ClN$_2$O$_4$Pd: C, 43.76; H, 2.98; N, 6.38%).

| 11 | 1.01 | 2,9-dimethyl-1,10-phenanthroline (1.45) | CH$_3$CN (25) room temp. | N.D. | orange |

Found: H, 4.09; N, 6.38, Pd, 24.8. Calc. for C$_{18}$H$_{18}$N$_2$O$_4$Pd: H, 4.19; N, 6.47; Pd, 24.59%).

| 12 | 0.98 | 5-methyl-1,10-phenanthroline (2.06) | CH$_3$CN (25) | 0.79 | yellow |
| 13 | 0.99 | 4-methyl-1,10-phenanthroline (2.14) | Et$_2$O (25) room temp. | N.D. | yellow |

N.D. Not Determined

Examples 10 and 11 produced what are believed to be novel compounds confirmed by elemental analysis as reported in Table 1.

Catalyst solubility can be improved by increasing the molecular weight of the palladium carboxylate. This is shown by Examples 14–18.

EXAMPLE 14

Solubility of [1,10-phenanthroline]Pd(OAc)$_2$: To a round bottom flask equipped with a thermometer, reflux condenser and magnetic stirrer was charged vinyl acetate (25.9 g, 301 mmol) and [1,10-phenanthroline]Pd(OAc)$_2$ (0.15 g, 0.37 mmol). The temperature was increased to 60° C. The complex did not dissolve in the vinyl acetate at 60° C.

EXAMPLE 15

Preparation of palladium stearate: To a round bottom flask was added stearic acid (1.09 g, 3.84 mmol) and Pd(OAc)$_2$ (0.39 g, 1.74 mmol). Temperature was increased to melt the stearic acid and held for 2 hours The melt was cooled to room temperature, dissolved in 200 ml hexane and filtered to remove any solids. The hexane solution was washed with 2×20 ml 2% NaOH, 20 ml distilled water and the hexane phase was dried over Na$_2$SO$_4$. The hexane was removed on a roto-vac. The dried palladium stearate (0.89 g, 1.32 mmol) had the following characteristic IR bands: 2920, 2850, 1600, 1410 cm$^{-1}$.

EXAMPLE 16-17

General Procedure: A round bottom flask was charged with solvent, palladium stearate and ligand. After a 2 hour reflux, the slurry was cooled to room temperature and the complexes isolated by filtration. Table 2 summarizes the results.

TABLE 2

Palladium Stearate Complexes with Aryl N-containing Ligands

| Ex | Pd (stearate)$_2$ (mmol) | Ligand (mmol) | Solvent (ml) | Complex (mmol) | Color | IR |
|---|---|---|---|---|---|---|
| 16 | 0.36 | 1,10-phenanthroline 0.39 | CH$_3$CN (30) | 0.16 | yellow | 2920, 2850, 1625 |
| 17 | 0.17 | pyridine 3.33 | hexane (20) room temp. | 0.15 | light yellow | 2920, 2840, 1625, 1600 |

EXAMPLE 18

Solubility of [1,10-phenanthroline]Pd(stearate)$_2$: In a similar fashion as in Example 14, vinyl acetate (12.9 g, 150 mmol) and [1,10-phenanthroline]Pd(stearate)$_2$ (0.1 g, 0.12 mmol) were heated until dissolution. Dissolution occurred between 45°–60° C.

EXAMPLE 19-33

Examples 19–33 demonstrate catalytic activity for the palladium complexes while a comparison of Examples 32 and 33 show the remarkable activity increase resulting from the addition of a strong acid.

General Procedure: To a 3-necked 100 ml round bottom flask equipped with a thermometer, reflux condenser and magnetic stirrer was charged vinyl acetate (12.9 g, 150 mmol) and stearic acid (2.8 g, 9.9 mmol). The contents of the flask were heated to 65° C. When the mixture reached 45° C., the stearic acid dissolved. Catalysts were added at 65° C. and aliquot samples withdrawn at 0, 30, 60, 90 and 180 minutes. Each solution was evaporated under a stream of N$_2$ to remove the vinyl acetate (IR band at 1370 cm$^{-1}$ missing). A plot of $A_{RCO2H}/(A_{RCO2H}+A_{vinylic})$ was plotted against time to yield a line. Activity comparisons were based on the linear part of the line covering at least 2-3 half-lives. Table 3 summarizes the activity comparisons.

TABLE 3

Palladium Acetate Complexes for Transvinylation of Stearic Acid

| Ex | Complex (mmol) | Activity $[A_{RCO2H}/(A_{RCO2H}+A_{vinylic})]$ Per Min. | Comment |
|---|---|---|---|
| 19 | [2,2'-biquinoline]Pd(OAc)$_2$ (0.19) | 3.4 × 10$^{-3}$ | — |
| 20 | [2,2'-dipyridyl]Pd(OAc)$_2$ (0.19) | 9.2 × 10$^{-3}$ | |
| 21 | [isoquinoline]$_2$Pd(OAc)$_2$ (0.18) | 5.3 × 10$^{-3}$ | Soln. went from yellow to blue |
| 22 | [pyridine]Pd(OAc)$_2$ (0.18) + pyridine (12.4) | 1.2 × 10$^{-3}$ | Soln. stayed yellow |
| 23 | [1,10-phenanthroline]Pd(OAc)$_2$ (0.18) | 8.9 × 10$^{-3}$ | Soln. stayed yellow |
| 24 | [3,4,7,8-tetramethyl-1,10-phenanthroline]Pd(OAc)$_2$ (0.18) | 7.7 × 10$^{-3}$ | Soln. stayed yellow |
| 25 | [2,9-dimethyl-4,7-diphenyl-1,10- | 1.8 × 10$^{-3}$ | Soln. turned red |

TABLE 3-continued

Palladium Acetate Complexes for Transvinylation of Stearic Acid

| Ex | Complex (mmol) | Activity [A$_{RCO_2H}$/(A$_{RCO_2H}$ + A$_{vinylic}$) Per Min. | Comment |
|---|---|---|---|
|  | phenanthroline]Pd(OAc)$_2$ (0.17) |  |  |
| 26 | [4,4'-diphenyl-2,2'-dipyridyl]Pd(OAc)$_2$ (0.19) | 4.4 × 10$^{-3}$ | Soln. stayed yellow |
| 27 | [4,7-diphenyl-1,10-phenanthroline]Pd(OAc)$_2$ (0.19) | 18.6 × 10$^{-3}$ | Soln. stayed yellow |
| 28 | [5-methyl-1,10-phenanthroline]Pd(OAc)$_2$ (0.19) | 16.8 × 10$^{-3}$ | — |
| 29 | [4-methyl-1,10-phenanthroline]Pd(OAc)$_2$ (0.19) | 10.3 × 10$^{-3}$ | Soln. stayed yellow |
| 30 | [5-chloro-1,10-phenanthroline]Pd(OAc)$_2$ (0.19) | 14.5 × 10$^{-3}$ | — |
| 31 | [2,9-dimethyl-1,10-phenanthroline]Pd(OAc)$_2$ (0.19) | 2.4 × 10$^{-3}$ | Soln. stayed yellow |
| 32 | [pyridine]$_2$Pd(OAc)$_2$ (0.18) | 3.6 × 10$^{-3}$ | Soln. went from yellow to blue |
| 33 | [pyridine]$_2$Pd(OAc)$_2$ (0.19) H$_2$SO$_4$ (0.71 mmol) | 25.0 × 10$^{-3}$ | — |

A strong comparison of Examples 32 and 33 shows that the addition of a strong acid resulted in a seven-fold increase in activity. Examples 30 and 31 demonstrate catalytic effectiviness for the novel palladium complexes of Examples 10 and 11, respectively.

EXAMPLES 34–40

In a similar fashion as in Example 19–33, other catalyst precursors were tested for transvinylation activity. Table 4 summarizes the comparative examples.

TABLE 4

Palladium Complexes for Transvinylation of Stearic Acid

| Ex | Complex (mmol) | Comment |
|---|---|---|
| 34 | (Ph$_3$P)$_2$PdCl$_2$ (0.19) | No transvinylation. |
| 35 | (Ph$_3$P)$_2$Pd(OAc)$_2$ (0.18) | Original yellow complex in heated reaction solution turned red. No transvinylation. |
| 36 | [Rh(OAc)$_2$]$_2$ (0.18) | No transvinylation. |
| 37 | (Ph$_3$P)Rh(OAc)$_2$ (0.12) | Original orange complex in heated reaction solution turned blue. No transvinylation. |
| 38 | cis-dichloro(2,2'-dipyridyl) ruthenium (0.19) | No transvinylation. |
| 39 | [2,2'-dipyridyl]Pd(O$_2$CCF$_3$)$_2$ (0.18) | 0.5 × 10$^{-3}$ (as defined in Table 3) (very slow). |
| 40 | [1,10-phenanthroline]PdCl$_2$ (0.18) | No transvinylation. |

EXAMPLE 41–53

In a similar fashion as in Examples 19–33, dibasic organic acids were subjected to transvinylation conditions and these results are summarized in Table 5.

TABLE 5

Transvinylation of Dibasic Acids

| Ex | Complex (mmol) | Vinyl Acetate (mmol) | Acid (mmol) | Activity* |
|---|---|---|---|---|
| 41 | [1,10-phenanthroline]Pd(OAc)$_2$ (0.18) | 600 | suberic acid (9.9) | No rxn. |
| 42 | [2,2'-dipyridyl]Pd(OAc)$_2$ (0.19) | 301 | adipic acid (10.1) | No rxn. |
| 43 | [1,10-phenanthroline]Pd(OAc)$_2$ (0.18) | 459 | adipic acid (7.6) | No. rxn. |
| 44 | [pyridine]$_2$Pd(OAc)$_2$ (0.19) H$_2$SO$_4$ (0.86) | 457 | adipic acid (7.6) | 4.9 × 10$^{-3}$ |
| 45 | [pyridine]$_2$Pd(OAc)$_2$ (0.19) | 461 | adipic acid (7.6) | 2.6 × 10$^{-3}$ |
| 46 | [pyridine]$_2$Pd(OAc)$_2$ (0.18) H$_2$SO$_4$ (0.82) | 291 | adipic acid (6.9) | 8.9 × 10$^{-3}$ |
| 47 | [4,7-diphenyl-1,10-phenanthroline]Pd(OAc)$_2$ (0.18) H$_2$SO$_4$ (0.82) | 291 | adipic acid (6.8) | 2.9 × 10$^{-3}$ |
| 48 | [pyridine]$_2$Pd(OAc)$_2$ (0.19) H$_2$SO$_4$ (0.86) | 300 | suberic acid (9.8) | 9.4 × 10$^{-3}$ 79% isolated yield |
| 49 | [pyridine]$_2$Pd(OAc)$_2$ (0.19) H$_2$SO$_4$ (0.85) | 395 | glutaric acid (9.8) | 5.9 × 10$^{-3}$ |
| 50 | [pyridine]$_2$Pd(OAc)$_2$ (0.19) H$_2$SO$_4$ (0.86) | 300 | succinic acid (10.2) | 8.8 × 10$^{-3}$ |
| 51 | [pyridine]$_2$Pd(OAc)$_2$ (0.19) Amberlyst 15 (0.94) | 233 | adipic acid (7.2) | 8.6 × 10$^{-3}$ |
| 52 | [pyridine]$_2$Pd(OAc)$_2$ (0.19) p-toluenesulfonic acid (0.79) | 233 | adipic acid (7.7) | 3.8 × 10$^{-3}$ |
| 53 | [pyridine]$_2$Pd(OAc)$_2$ (0.19) p-toluenesulfonic acid (1.65) | 233 | adipic acid (7.5) | 7.0 × 10$^{-3}$ |

*As defined in Table 3
**Amberlyst 15 ® resin is cross-linked polystyrene sulfonic acid resin The above results show significant increase in catalyst activity for transvinylation of dibasic acids when a strong acid was added to the system.

EXAMPLE 54

Preparation of divinyl adipate: In a 3-necked 1000 ml round bottom flask equipped with a reflux condenser, thermometer and magnetic stirrer was added vinyl acetate (320 g, 3791 mmol), adipic acid (17.5 g, 120 mmol), [pyridine]$_2$Pd(OAc)$_2$ (1.2 g, 3.1 mmol) and p-toluenesulfonic acid (4.4 g, 25.6 mmol). The temperature was held at 65° C. for 4 hours. After cooling to room temperature, NaOAc (3.0 g) was added to the solution. Volatiles were removed by a roto-vac. The non-volatiles were diluted with 200 ml hexane, extracted with 2×100 ml 2% NaOH, extracted with 100 ml distilled water and then dried over Na$_2$SO$_4$. The hexane was removed with a roto-vac. TLC showed on component. The divinyl adipate weighed 23.7 g (99.7% yield). IR(NaCl plate): 2940, 1750, 1640, 1370 cm$^{-1}$.

EXAMPLE 55

In a 50 ml round bottom flask equipped with a reflux condenser was added acetonitrile (25 ml), palladium acetate (0.2 g, 0.89 mmol) and dried Reillex ® 425 (1.0 g, 7.1 mmol). The slurry was refluxed for 8 hr. upon cooling to room temperature the beads were filtered and washed with 10 ml acetonitrile. The resin was dried in a vacuum oven for 3 hrs. at 100° C. under N$_2$. The dried beads weighed 1.18 g. Reillex ® 425 is a cross-linked polyvinylpyridine available from Reilly Tar and Chemical Company.

EXAMPLE 56-57

In a similar fashion as in Example 19-33, the resin supported Pd(OAc)$_2$ of Example 55 was treated to transvinylation conditions with vinyl acetate (12.9 g, 150 mmol) and stearic acid (2.8 g, 9.9 mmol). Results are summarized in Table 6.

TABLE 6

| Reillex ® 425-Pd(OAc)$_2$ Complex for Transvinylation | | |
| --- | --- | --- |
| Ex | Complex (mmol) | Activity* |
| 56 | Reillex ® 425-Pd(OAc)$_2$ (0.45)** | 1.8 × 10$^{-3}$ |
| 57 | Reillex ® 425-Pd(OAc)$_2$ (0.45) p-toluenesulfonic acid (1.45) | 7.9 × 10$^{-3}$ |

*As defined in Table 3
**0.6 g of beads prepared in Example 55

These results show over a four-fold increase in activity with the addition of a strong acid to the system.

Other embodiments and advantages of our invention will be apparent to those skilled in the art from the foregoing disclosure without departing from the spirit or scope of the invention.

I claim:

1. In a process for transvinylation of a vinyl ester with an alcohol or a carboxylic acid using a palladium catalyst introduced to the reaction mixture as a palladium carboxylate complexed with an aryl N-containing ligand, the improvement comprising adding to the reaction mixture a sulfur oxy-acid or sulfur oxy-acid mixture having a Hammett acidity ($-H_o$) of greater than 0.8.

2. The process of claim 1 wherein said acid is sulfuric acid.

3. The process of claim 1 wherein said acid is p-toluenesulfonic acid.

4. The process of claim 1 wherein said acid is a cross-linked polystyrene sulfonic acid resin.

5. The process of claim 1 wherein said palladium carboxylate is palladium acetate.

6. The process of claim 1 wherein said vinyl ester is vinyl acetate.

7. A process for transvinylation between a vinyl ester and a carboxylic acid which comprises contacting said ester and carboxylic acid under reaction conditions in the presence of a catalyst added to the reaction system as an aryl N-containing ligand complex of palladium acetate and adding a sulfur oxy-acid or sulfur oxy-acid mixture having a Hammett acidity ($-H_o$) of greater than 0.8.

8. The process of claim 7 wherein said carboxylic acid is a mono-basic acid.

9. The process of claim 7 wherein said carboxylic acid is a di-basic acid.

10. The process of claim 7 wherein said vinyl ester is selected so that its acid moiety liberated in the reaction has a lower boiling point than said carboxylic acid and said liberated acid is removed from the reaction system during the course of the reaction by distillation.

11. The process of claim 7 wherein said vinyl ester is vinyl acetate.

12. The process of claim 7 wherein said aryl N-containing ligand complex of palladium acetate is 5-chloro-1,10-phenanthroline complexed with palladium acetate.

13. The process of claim 7 wherein said aryl N-containing ligand complex of palladium acetate is 2,9-dimethyl-1,10-phenanthroline complexed with palladium acetate.

* * * * *